(12) United States Patent
Kenefick et al.

(10) Patent No.: US 6,591,679 B2
(45) Date of Patent: Jul. 15, 2003

(54) METHOD FOR SIZING SURFACE BREAKING DISCONTINUITIES WITH ULTRASONIC IMAGING

(75) Inventors: Steven A. Kenefick, Charlotte, NC (US); Gary L. Henry, Charlotte, NC (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 46 days.

(21) Appl. No.: 09/992,398

(22) Filed: Nov. 14, 2001

(65) Prior Publication Data

US 2003/0089171 A1 May 15, 2003

(51) Int. Cl.$^7$ .................................................. G01H 5/00
(52) U.S. Cl. ..................................................... 73/597
(58) Field of Search ........................... 73/570, 579, 588, 73/589, 596, 597, 598, 620, 621, 622; 702/34, 35, 36, 41, 42, 43

(56) References Cited

U.S. PATENT DOCUMENTS 4,947,351 A * 8/1990 Moran et al. .................. 702/39
5,582,173 A * 12/1996 Li .......................... 128/660.07
5,750,895 A * 5/1998 Chern et al. ................... 73/614

\* cited by examiner

*Primary Examiner*—Richard A. Moller
(74) *Attorney, Agent, or Firm*—Armstrong, Westerman & Hattori, LLP

(57) ABSTRACT

Ultrasonic scan data is displayed within a display (10) and is arranged in a plurality of two and three-dimensional colored displays (20, 30, 40, 50). A C-scan display (40) is a composite plot of a region of interest using color to designate echo amplitude. The composite plot (40) is time-gated to limit the range of depths of data presented and thereby limit the plot to a thin section such as a surface. Surface breaking discontinuities (100) are visible as highly colored echoes within this C-scan display (40). Within C-scan display (40), once a discontinuity such as a reflector is detected, additional gates (150–165) may be set which permit other specialized displays such as D-scan (50) and B-scan (20) windows to portray the discontinuities. The D-scan plots index direction (54) against time (52), and readily displays circumferential reflectors (130–145) therein, while also enabling rapid estimation of the depth (142) of these reflectors. A B-scan plot (20) which enables fine profilming of reflectors may be a single pane taken at a single axial location determined by an index cursor (168), or may alternatively be a composite plot. Various modifications to the basic system are disclosed that further enhance the utility of the display (10).

37 Claims, 4 Drawing Sheets

METHOD FOR SIZING SURFACE BREAKING DISCONTINUITIES WITH ULTRASONIC IMAGING

BACKGROUND OF THE INVENTION

1. Field of the Invention

The present invention pertains generally to the field of non-destructive testing of materials, and in one more particular manifestation to a method of examining conduits to more rapidly and precisely detect and measure flaws.

2. Description of the Related Art

There are many industrial and commercial applications where a material is most desirably tested, prior to being placed in service or subsequent thereto. In such instances, non-destructive testing methods are required which enable rapid and reliable testing and evaluation. Ultrasonic examination is one such method which has been applied successfully, particularly with metal materials, though not as well as still desired.

One particular industrial application where ultrasonic testing has proven to be of great value is the testing of heat exchanger tubes such as are used in electric power plants. Plant efficiency and consequent profits can be reduced by removing heat exchanger tubes from service. However, placing or leaving a defective tube in operation in a nuclear power plant could result in radioactive contamination. Using ultrasonic examination, the tubes may be tested even when they are of great length and generally independent of whether they are straight, bent or coiled. Testing may be done prior to placing tubes into service, to identify processing-related discontinuities that have arisen during manufacturing, or after tubes are in service to detect service-related discontinuities. One example of a service related discontinuity is an Outside Diameter Stress Corrosion Crack (ODSCC) which may extend from the outer diameter of a tube towards the inside diameter.

While discontinuities may require replacement of tubes, not all discontinuities are actually detrimental to continued operation. Consequently, analysis will most preferably be conducted to determine whether a reflector exceeds a critical dimensional limit, or is instead deemed acceptable. Detecting service-related discontinuities in advance of a failure is highly desired, which enables timely replacement or taking the tubes out of service. These tubes are frequently not readily removed from service, and so are most preferably tested prior to installation, and then at intervals between periods of use on location. With such timely detection and sizing of reflectors, the tubes will only be installed when satisfactory, and later replaced or taken out of service only when necessary.

Components used in ultrasonic examination and applicable to various degree to the present invention are known in the industry. These components may, for example purposes, consist of ultrasonic signal generator and receive instrumentation, a search unit containing at least one ultrasonic transducer, cabling, data recording equipment and data analysis software. The signal generator creates high-frequency electric pulses that are transmitted through the cabling to the search unit. The search unit will preferably contain at least one piezoelectric crystal or equivalent transducer that converts high-frequency electric pulses into ultrasonic mechanical vibrations. A liquid which has a relatively high efficiency of transmission, will typically serve to couple the transducer to the material to be tested.

Typically, ultrasonic energy generated by the transducer is transmitted by compression wave to the material, and will strike the material at a particular angle of incidence. Generally, a normal angle of incidence will result in reflection from the material back to the transducer, and further reflection from the transducer leading to a bouncing back and forth. However, when the angle of incidence is different from normal (perpendicular) to the surface, part of the energy is refracted in the tube wall, and the incident compression wave is converted into a shear wave within the material. The angle of fraction is governed by Snell's law and depends on the wave velocity of the liquid and the material under test.

In the case of a cylindrical tube or other material with parallel surfaces of the wall, the refracted shear wave will continue to propagate in the material, in the absence of defects and surface irregularities, by successively bounding between outer and inner surfaces. The propagation of ultrasonic energy in material without parallel wall sides or which is not cylindrical can also be predicted and is contemplated herein, but is not specifically addressed herein to avoid further complicating an understanding of the operation of the present invention. In all cases, the refracted shear wave will continue to propagate in the material until dissipated by various mechanisms such as scatter, attenuation, refraction and diffraction.

When a shear wave encounters a defect or material discontinuity, the refracted shear wave interacts with the defect differently. The defect acts as an internal reflector, and so disrupts the internal propagation and dissipation. There are normally two detectable interactions between refracted shear wave and reflectors that are particularly important to the present invention. One is the corner reflection or echo, and the other is the tip echo.

When the ultrasonic wave hits the root of the crack, the corner formed by the tube wall and the crack root will reflect a portion of the energy. This echo, referred to generally as the corner echo, travels back to the transducer for conversion into a corner signal. Typically, this corner signal is relatively strong and readily detected. There will be a measurable amount of time between generation of the wave and receipt of the echo at the transducer. The amount of time delay is directly related to the distance of travel of the wave in the material, and so the location of the reflector may be readily calculated.

When the ultrasonic wave hits the tip of a crack, the wave front will bend around the tip of the crack. This phenomenon is known as diffraction. The diffracted wave will produce a radial propagating wave with its center at the crack tip, producing a tip echo that is detected by the transducer and converted into a tip signal. The tip signal is generally a weaker signal than the corner signal, and can be much more difficult to distinguish from background noise. Nevertheless, and like the corner signal, there will be a time delay between generation of wave and receipt of echo which can be used to calculate the location of the tip.

After the ultrasonic waves are reflected back to the transducer, or to another receiver, the receiver converts the wave into an electrical signal. This signal is typically presented or displayed as an A-scan, which plots time on one axis (typically the X-axis) and signal amplitude on the other axis. Where the X-axis represents time, the horizontal distance between any two signals represent the material distance between the two conditions causing the signals. Using one prior art technique, an inspector moves a search unit along a material under test, while simultaneously interpreting the A-scan signals on a portable ultrasonic instrument. The corner and tip signals are identified, and the separation in arrival time between these two signals, represented by an X-axis displacement between the two signals, is used to calculate the depth of the reflector. This type of inspection requires tremendous training and expertise to accurately interpret the A-scan displays, and a great deal of dexterity and patience to thoroughly evaluate a reflector. Consequently, the prior techniques have not produced by intuitive and rapid sizing technique.

As an improvement thereto, computer aided examinations have been devised by the present inventors to include the acquisition and storage of signal time delay, amplitude and transducer position through a large number of transducer positions. The data is then analyzed either in real time or later, using data analysis software. This computer aided examination allows the data to be analyzed in different ways and by different persons. However, the examination has heretofore consumed more time and has been more difficult than desired.

SUMMARY OF THE INVENTION

In a first manifestation, the invention is a method for inspecting a reflector in a material using a non-destructive ultrasound inspection technique which simultaneously decreases the time required for inspection and also improves the quality of inspection. According to the method, an ultrasonic transducer is moved relative to the material through a range of positions within two axes of motion. The ultrasonic transducer is fired at precise locations within the range, and an ultrasonic echo from the material is received back. The ultrasonic echo is converted to an electrical signal having an amplitude representing a strength of the echo. The time difference between firing and receiving an echo is measured. A two-dimensional map of the material is displayed in a planar C-scan view by displaying a time-gated plot of one of two axes against the other, and using a coding scheme to identify relative amplitudes within the plot. A reflector region of interest is determined within the C-scan, and has a first axial starting location on a first axis, a first axial ending location on the first axis, a second axial starting location on a second axis, and a second axial ending location on the second axis. Received echo signal data within the gated reflector region of interest is plotted using the second axis position plotted against time difference, using the coding scheme to identify relative signal amplitudes within the plot to produce a D-scan.

In a second manifestation, the invention is a method for analyzing recorded ultrasound data. The various steps include: representing recorded ultrasound data using one axis position as one of an abscissa or an ordinate on a Cartesian graph; depicting a magnitude of time as the other of the abscissa or ordinate on a Cartesian graph; plotting recorded ultrasound data using axis position representation and time difference depiction; and color coding a relative amplitude of data within the plot.

In a third manifestation, the invention is a method for inspecting heat exchanger tubing at discrete times prior to installation and in-situ. According to this manifestation, an ultrasonic transducer passes helically through the tubing, generating ultrasonic pulses at a plurality of circumferential and axial locations. Ultrasonic echoes from the tubing are converted to an echo electrical signal having an amplitude representing a strength of the echoes. The echo electrical signal is transmitted to a signal processor for subsequent processing, calculation and display. A time difference is measured between generating and receiving echoes. The measured time difference is translated into an equivalent material depth within the heat exchanger tubing by using the signal processor, a known ultrasonic wave angle-of-incidence, and a known ultrasonic wave velocity within the tubing. A two-dimensional map of the tubing in a planar C-scan view is displayed by plotting an ultrasonic wave transit distance gated plot of circumferential angle against axial displacement. A visual characteristic of the two dimensional map correlates to relative amplitude, to operatively enable a viewer to identify echo amplitudes within the map. The extent of a reflector within the tubing is determined, including starting and ending angles on a circumference of the tubing, and axial starting and ending locations of the reflector along a longitudinal axis of the tubing. The echo electrical signal is graphed using circumferential angle plotted against ultrasonic wave transit distance to thereby produce a D-scan. A visual characteristic of the D-scan conforms to a relative amplitude of echo electrical signal, to operatively enable a viewer to identify echo electrical signal amplitudes within the D-scan. Within the D-scan, the inspector selects a starting location of the reflector which represents a singular axial position. This singular axial position is used to map the echo electrical signal circumferential angle plotted against ultrasonic wave transit distance. This map is for all events where the received echo is received from this singular axial position, to produce a B-scan. Visual features are matched with echo electrical signal amplitudes within the B-scan to operatively enable a viewer to identify echo electrical signal amplitudes therein.

OBJECTS OF THE INVENTION

Exemplary embodiments of the present invention solve inadequacies of the prior art by providing a non-destructive ultrasonic examination analysis method to characterize ultrasonic reflectors such as cracks, defects, flaws, intended features including welds, grooves, machined features, material junctions and other ultrasonic reflectors that may be present in a material. The method is based on generation and analysis of specific and highly beneficial images created from ultrasonic scans.

A first object of the invention is to reduce the time required to non-destructively test a material. A second object of the invention is to enable an inspector to accurately characterize reflectors by orientation, length, depth and profile, all with less adverse effects from background noise than heretofore available. A further object of the invention is to enable data to be collected and then analyzed at a later time period or by a plurality of inspectors. Yet another object of the present invention is to allow the inspector to gate data to particular ranges of interest, thereby limiting the amount of extraneous information being displayed in any given window. A still further object of the invention is to enable much more data to be displayed in a single window than was heretofore possible through a composite display and with visual amplitude representation.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

Figure 1:
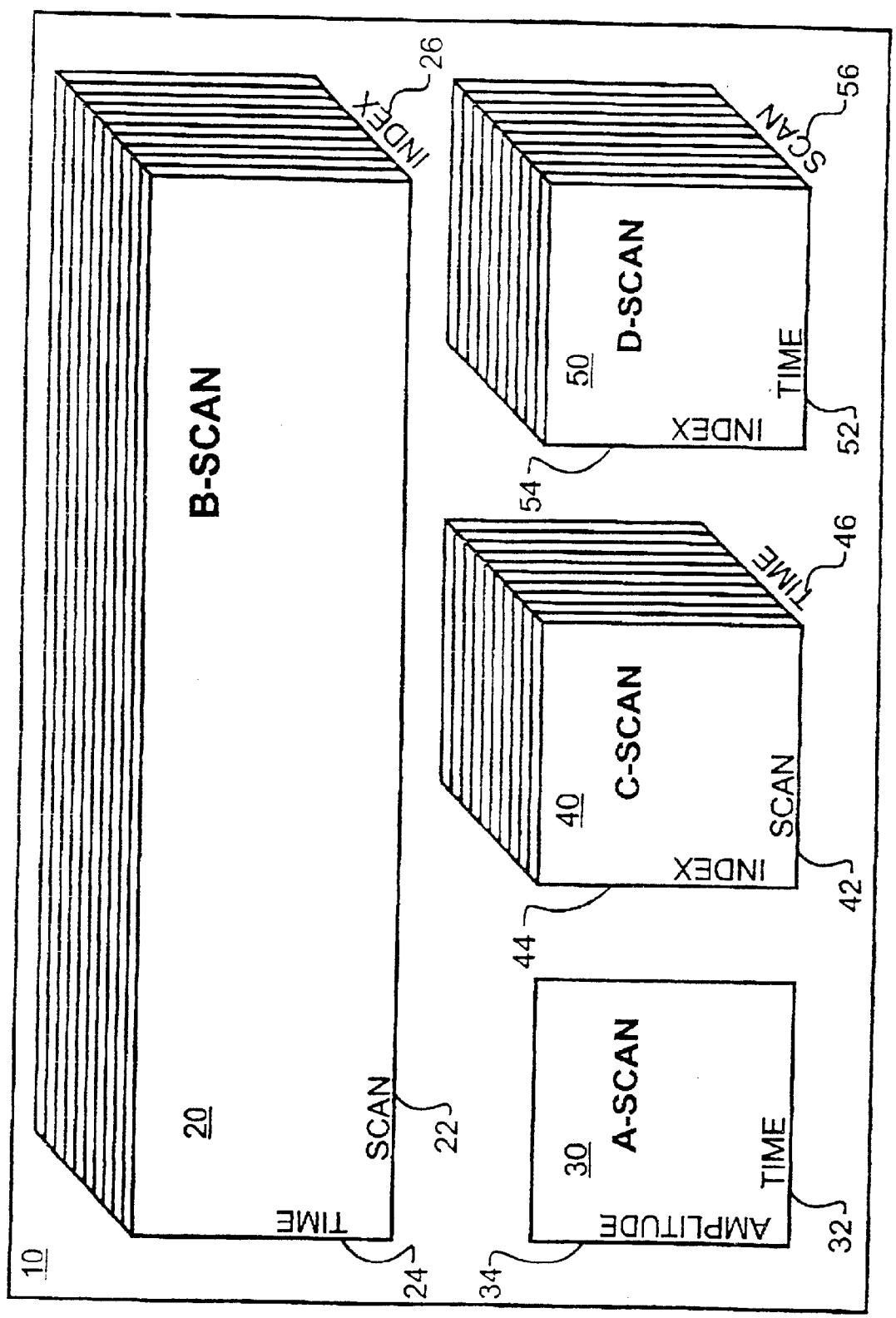
FIG. 1 illustrates a most preferred display organization schematically, arranged in accord with the teachings of the present invention.

Manifested in the preferred embodiment, which is given to illustrate the invention rather than to limit its scope, the present invention provides a simplified and more rapid method for locating and sizing reflectors in a material. The preferred display 10 is organized as illustrated schematically in FIG. 1, where various measured scan data are arranged in a highly beneficial manner. For the purpose of the present description, which uses a circumferential crack for illustrative purposes, scan direction is parallel to the crack, or circumferential. Index direction is perpendicular or normal thereto, or parallel to the tube axis. Those skilled in the art will recognize, however, that the data may be acquired in different ways and named differently, such that scan direction and index direction may change in orientation or naming, without altering the present inventive method.

Four scans are illustrated within display 10, including B-scan 20, A-scan 30, C-scan 40, and D-scan 50. The B, C and D-scans are generated by data analysis software used for this application from A-scan amplitude data that is gathered at distinct physical locations of the ultrasonic transducer. B-scan 20 plots scan direction on X-axis 22, which, for a tube having an exemplary circumferential reflector, is the angle of rotation about the tube circumference. Time is plotted on Y-axis 24, and index direction, which corresponds to axial position along the tube, on Z-axis 26. Most preferably, A-scan 30 plots time on X-axis 32 and signal amplitude on Y-axis 34. C-scan 40 plots scan direction on X-axis 42, index direction on Y-axis 44, and time on Z-axis 46. D-scan 50 plots time on X-axis 52, index direction on Y-axis 54, and scan direction on Z-axis 56. Other supplemental scans may be displayed as well, and the placement and orientation of scans will be determined by those skilled in the art at the time of design or utilization of the present invention. For the purposes of the present exemplary embodiment, only these four scans will be discussed. In addition, the data analysis software will most preferably be programmed to process measured transit time into an equivalent material depth, which for display purposes is presented herein as time, by providing constants to the software in advance including the ultrasonic wave angle and wave velocity within the material, and then calculating the material depth from these and the measured transit time using known equations.

While display 10 in the most preferred embodiment will comprise a video display such as a computer monitor screen or the like, and will therefore be a two-dimensional display not technically capable of displaying the Z-axis, the present invention most preferably provides the user the option to use composite images that present multiple Z-axis single pane images together as a single composition image. While a single pane image provides the advantage of high resolution, only a limited amount of data is available for viewing, and so there will typically be a need for both single pane and composite viewing options. The content of a composite image is controlled by selectively gating the range of Z-dimension data displayed within that view, the benefit which will become apparent herein below.

B, C and D-scan plots 20, 40, and 50 will also most preferably use some form of color coding, grey scale representation or the like within the plots to illustrate signal amplitude. The color pallet used to represent amplitude will most preferably and advantageously be selectable to emphasize particular portions of data, as will be described herein below. The exact colors or grey scales used are not critical to the invention, though it is most preferable to use colors which represent positive amplitude that are visually distinct from colors representing negative amplitudes for reasons also better explained herein below. As an example, but certainly not limiting the possibilities, positive signals can vary from green to blue to white as the amplitude signal increases, while negative signals can be represented from yellow to orange to red as the amplitude increases in the negative direction.

The data which is used to generate display 10 is gathered through an ultrasonic scan of the material, which in the exemplary embodiment is a tube. A helical scan is produced by rotating the search unit while pulling the search unit along the tube axis. Data is collected at precise angular and axial positions that are determined by axial and cimcumferential encoders or position sensors. At each precise position, an ultrasonic transducer is triggered. A resulting return signal is then processed, in order to generate C-scan display 40. The processing necessary in order to obtain the C-scan 40 illustrated in FIG. 2 includes gating the time dimension (Z-axis of C-scan 40) to include a time range that narrowly encompasses the time required for reflection from the surface of interest. In other words, if a tube is being examined for Outside Diameter Stress Corrosion Cracks (ODSCC), which extend from the outer diameter of a tube towards the inside diameter, then the time band of interest will include the average amount of time required for echoes from outside diameter surface irregularities and imperfections to be returned to the transducer. A small time window will normally be provided, meaning times slightly less and slightly greater than that average amount of time for signals returning from that surface will also be included in C-scan 40. C-scan 40 consequently provides a two-dimensional map proportion to the outer tube wall scanned area, in the exemplary embodiment having the angular position on the horizontal axis and the tube axis on the vertical axis. Ultrasound corner echoes from a circumferential crack will appear in alignment along the horizontal axis, while an axial crack will align along the vertical axis. In the case of a circumferential crack, as illustrated in the exemplary embodiment, the scan direction is then the angular rotation of the transducer and index direction is parallel to the tube cylindrical axis.

Figure 2:
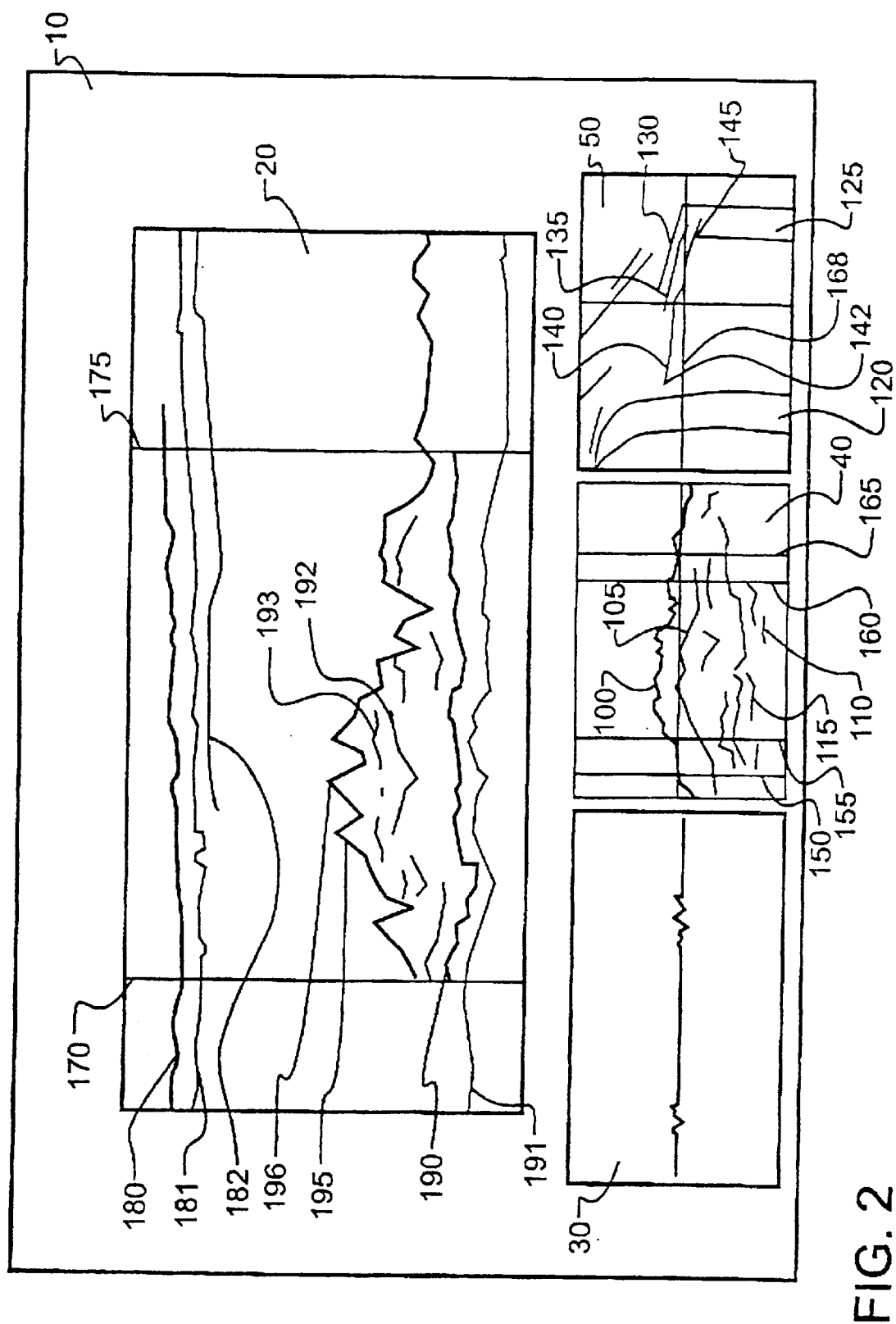
FIG. 2 illustrates a display organized in accord with the most preferred organization of FIG. 1, displaying data from a sample part having a crack which acts as a reflector.

As illustrated in FIG. 2, C-scan 40 will display corner echoes through amplitude contrast lines 100, 105. When a signal returned from an ultrasonic transducer has the greatest amplitude, this indicates that the ultrasonic transducer is closest to the reflector which is causing the ultrasonic reflection. Internal losses, including scatter, attenuation, refraction, reflection and diffraction, tend to reduce the amplitude of the reflected wave as distance from transducer to reflector increases. Consequently, the use of color or grey-scale representation of amplitude may help an inspector to visually distinguish in the C-scan the position of a reflector, as illustrated for exemplary purposes only by amplitude contrast lines 100, 105, from lower amplitude lines 110, 115.

Once the location of a reflector is identified in C-scan display 40, the data for display within B-scan 20 and D-scan 50 is in the most preferred embodiment further gated. Gating refers throughout this disclosure to one of various methods to select or limit the data displayed within a scan to data obtained from a limited range of values that are of interest. In the present exemplary figure, the C-scan data is limited to the outer surface of interest through time gating as already described herein above, while the D-scan data is limited to the index direction region where the reflector exists, and also to the time values that encompass the full width of the material wall. In the preferred embodiment, the index and scan gates are adjusted in the B, C, and D-scan display 40, and the gate values may be displayed together with a cursor, for example, on display 10 by lines within the scan windows, such as lines 150–165 of C-scan 40, and line 168 of D-scan 50. Lines 170–175 of B-scan 20 are measurement cursors. The selection of whether to display these lines 150–168 that represent gating limits and on-screen cursor is a design choice, but is preferred herein for ease of use. Most preferably, the index direction gate is set in the D-scan and the scan gate in the B-scan. The scan gate is set to encompass the reflector's corner signal where it intersects with the material outside wall signal. In B-scan 20 the scan direction gates are most preferably set to encompass the reflector length, plus preferably a few degrees on each end. The index gate in the D-scan is moved to intersect the reflector.

D-scan 50 of FIG. 2 displays the same reflector as C-scan 40 of FIG. 2, but this D-scan plots index direction against time. This exemplary illustrated D-scan is formed as a composite mode view, meaning that scan direction forms the Z-axis, and a plurality of single D-scans from different scan positions are compiled together as a single view. D-scan 50 allows an inspector, in a single display, the ability to make an incredibly rapid rough approximation of the depth of a reflector. As shown in FIG. 2, region 120 will typically have color grey scale amplitude lines that evidence one wall of the material being tested. This region may present amplitude excursions that are visible as long as D-scan 50 represents relative amplitudes by color, grey-scale or the like. Similarly, opposing wall 125 may also be visible, with amplitude excursions. Adjacent to wall region 125 is a corner signal or echo 145, which, like wall region 125, will generally have amplitude excursions. Extending from corner signal 145 are three crack tips 130, 135, 140. These crack tips 130–140 generally produce weaker tip signals, which can be difficult to separate from noise in the A-scan 30 display. However, when plotted as illustrated in D-scan 50 using a gated display, the tips are easily discerned. While it is possible to rapidly estimate the depth of crack tips 130–140 directly from D-scan 50, the precision available and lack of crack profile information is usually inadequate for an inspector to make a truly informed evaluation of a reflector. Consequently, it is preferable to use index cursor 168 to select a single index (z-axis) pane for display as B-scan 20.

In the single pane mode for B-scan 20 illustrated in FIG. 2, the use of amplitude representation using color or grey scale allows an inspector to readily visually discern lines which represent various physical features, similar to the D-scan display. In the case of B-scan 20, lines 180, 181, 182 represent echoes received from the wall designated by region 120 in D-scan 50. Wall signals and corner signals show up as visually discernable lines 190, 191, which are also typically accompanied by a large number of tip signals 192, 193. In most cases the corner echo will be measured as a maximum negative amplitude, while the tip signal will produce a maximum positive amplitude signal. Consequently, the use of visually distinct colors or grey scales for positive and negative amplitudes will allow this polarity difference to be more readily discerned.

The crack profile depth line 195 is established by the analyst and is based on the image generated by the tips. The extent of the tips can be identified in B-scan 20 based on color, grey scale or other visual indicator or coding, since where color is sued the color pallet most preferably represents different values for positive and negative portions of the signal. Noteworthy here is the fact that in the A-scan mode, a single small change in amplitude representing a tip signal is very difficult to correctly distinguish from noise. However, with a large number of data points plotted through the scan direction in the present B-scan 20, the correct identification of both noise and scan tips is greatly simplified, thereby vastly accelerating the inspection process and improving the overall quality of the results. The point of maximum reflector depth 196 for this single pane B-scan 120 is easily identified.

As aforementioned, any of the B, C, and D-scans will, in the preferred embodiment, be selected for either single pane mode or composite mode including a plurality of Z-axis plots overlaid upon each other. In the overlay mode, a general approximation of composite information, such as the maximum tip depth 142 from D-scan 50 of FIG. 2, may be easily had. Similarly, composites of B-scan 20 may be generated for a range of index values from the C or D-scan plots. This range may be useful to very rapidly estimate the largest tip values. The composites may be formed form half or full-wave rectified signals, thereby preventing cancellation of large amplitude signals by out-of-phase large amplitude signals. In general, a resulting composite scan will not be as accurate as a single pane view, but it will be much faster to review and evaluate.

Figure 3:
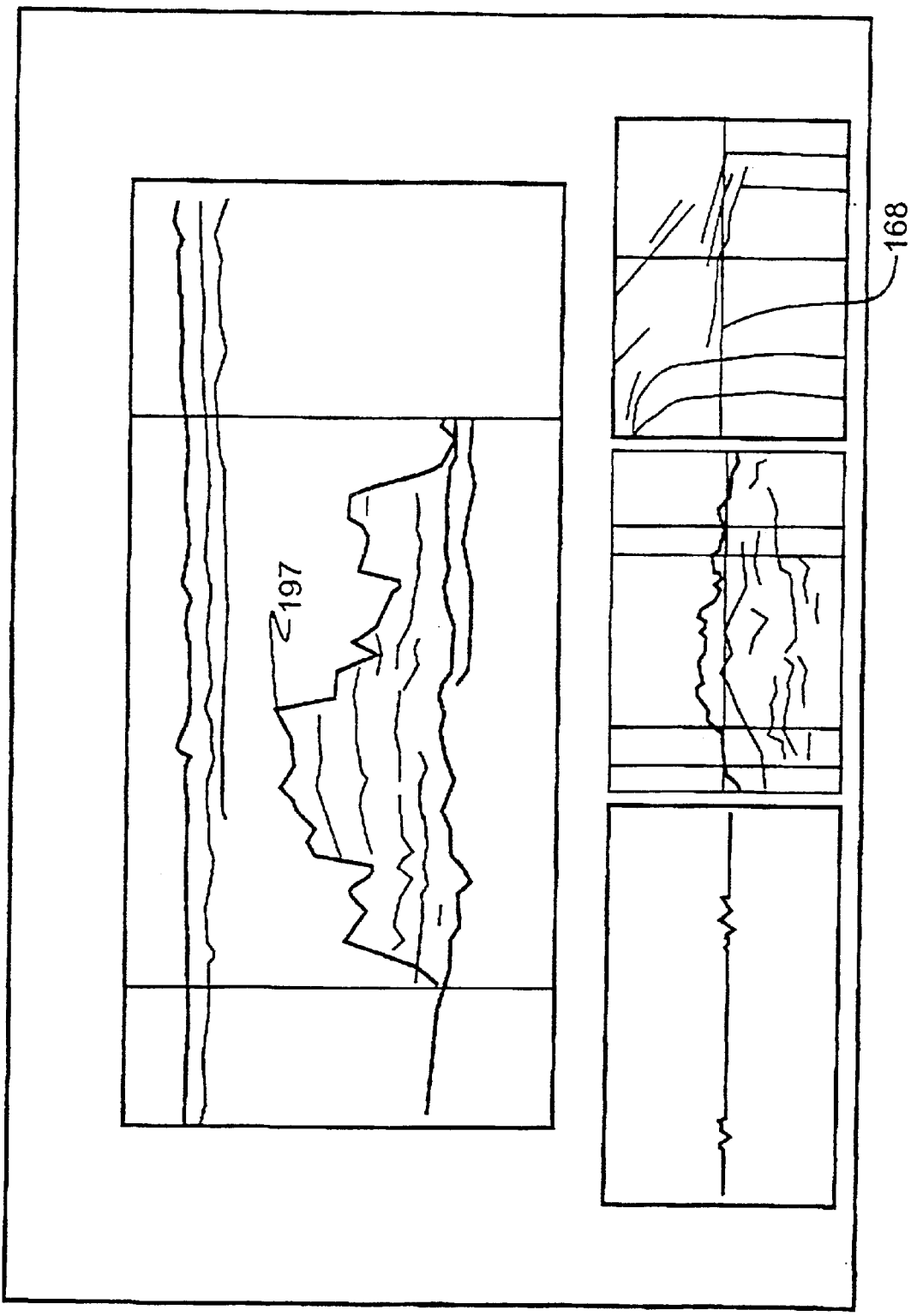
FIG. 3 illustrates the display of FIG. 2 with the horizontal index gate cursor moved toward a deeper portion of the crack tips.
Figure 4:
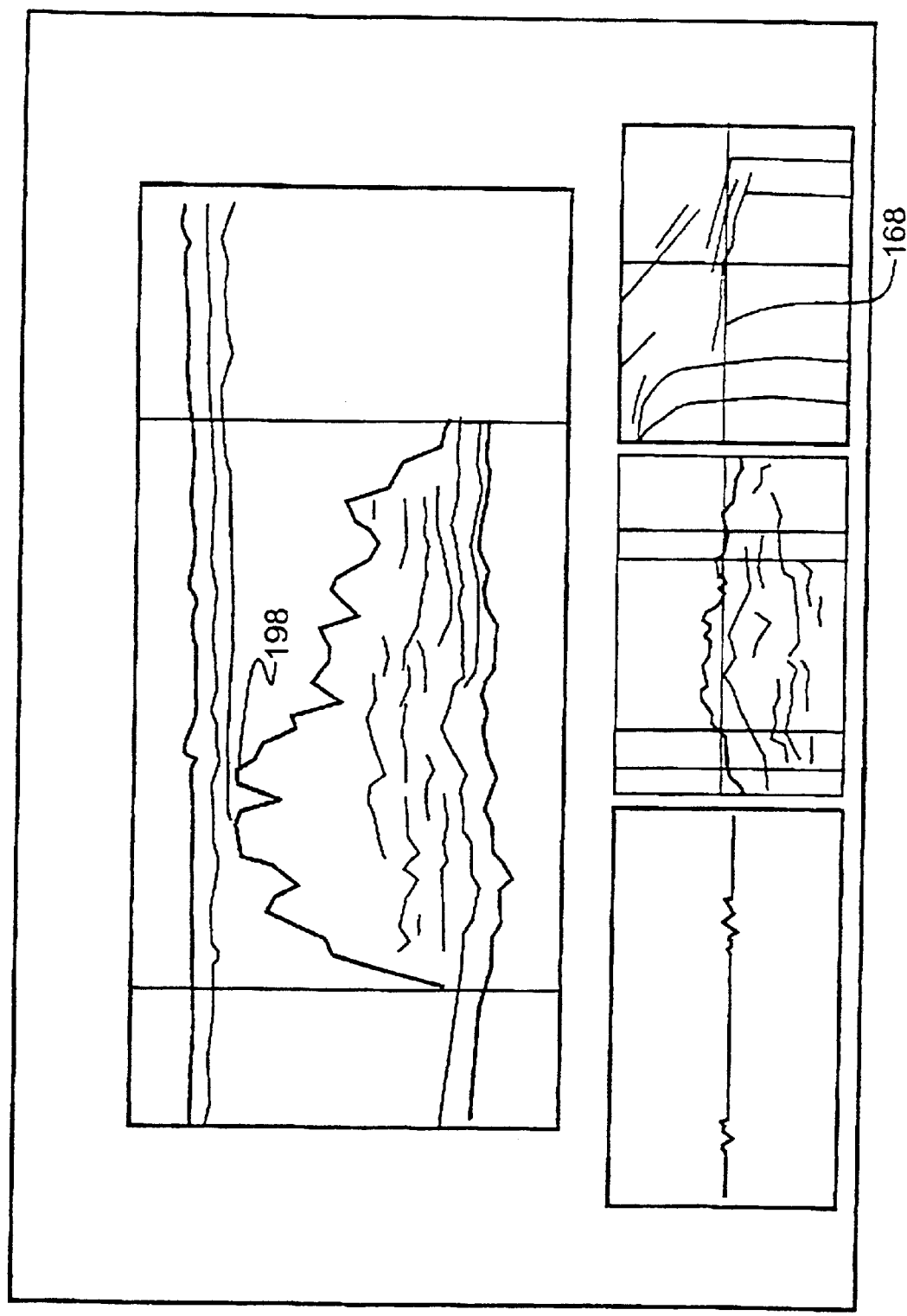
FIG. 4 illustrates the display of FIG. 3 with the horizontal index gate cursor moved toward a deeper portion of the crack tips, and showing the corner signal.

In order to benefit from the precision of a single pane view in B-scan 20, index cursor 168 will need to be moved through the range of index positions encompassing crack tips 130, 135, and 140. Using display 10 of FIG. 2, this would require index cursor 168 to be moved vertically, preferably incrementally. Each index position will reveal a new reflector profile and associated maximum reflector depth. The greatest reflector depth for each scan position will be the largest of the associated single pane maximum reflector depths for each position. FIGS. 3 and 4 illustrate the movement of the index cursor 168 to different locations, with the resulting changes to B-scans and the different single pane maximum reflector vanes 197, 198.

Once the deepest portion of the reflector has been identified, the base of the reflector corner is identified. This is done by placing the index cursor at the base of the reflector and moving through the corner signal. From this, the reflector corner location is identified.

To further enhance the performance of the preferred embodiment, a tip signal can be matched with a corner signal by using a 3-D cursor to measure the relative angle between corner and tip signals and confirm if the observed signals come from the same reflector ligament.

A method to further distinguish the corner and tip extent includes altering the color pallet. Typical corner images, which are normally negative mode signals, can be enhanced by changing the color pallet to display all positive signals as one color, while not changing the negative signal pallet. The resultant reduction in visual clutter simplifies the visual identification of the negative corner image. Similarly and as a separate step when the full pallet is restored, the tip signal can be enhanced by changing the color pallet to display all negative signals as one color, while leaving the positive color pallet unchanged.

Further enhancements are achieved by reducing the amplitude ranges displayed. For instance, if the threshold for most noise signal are at amplitudes of below one percent and the signal of interest is greater than one percent, the color pallet can be adjusted to only display from one to one hundred percent in the positive mode. This results in a clearer display of the low level positive signals. Further enhancements can be achieved by reducing the upper end of the display. It is important to note that this enhancement is generally most useful when the ranges are selected to maintain, and not eliminate, signals of interest.

As various data about a reflector is gathered, the data may be further saved or processed to be of value. For example, depth and circumferential positions of both tip and corner signals may be extracted to a spreadsheet or the like, where maximum depth, cracked area, percent cracked area and length may be calculated. In addition, a plot of the positions may be generated.

EXAMPLE

An Inconel tube having a ⅞" diameter, an 0.050" wall thickness, and a circumferential ODSCC of known size was scanned, using the circumferential direction as scan reference, and the length of the tube as the index reference. Ultrasonic RF data was collected from the tube using a 15 MHz forty-five degree focused search unit. The time gate used for production of the C-scan was adjusted to encompass the outside surface of the tube, and the results are illustrated in C-scan 40 of FIG. 2. Next, the index gates were adjusted in C-scan 40 to encompass the ODSCC, to produce a D-scan composite image 50 that presented the corner and associated tip signals for the entire ODSCC. An estimate was made, at that time, from the image displayed by D-scan 50, of the maximum overall depth of the ODSCC. The ODSCC was then purified in B-scan 20 by moving index gate 168 into and through the entire ODSCC signal presented in D-scan 50. The maximum initial positive mode location of the tip signal and the maximum initial negative mode for the corner signal were identified over the length of the ODSCC. Depth and circumferential positions of both tip and corner signals were extracted to a spreadsheet, where maximum depth, cracked area, percent cracked area, and length were calculated. The sample used for this example was then destructively tested metallurgically to measure the crack size. Table 1 provides a comparison of the present invention and metallurgical results.

TABLE 1

|  | Present Invention | Metallurgical |
| --- | --- | --- |
| ODSCC Area | 0.0171 in$^2$ | 0.0166 in$^2$ |
| ODSCC Length | 80 Degrees | 84 Degrees |
| Maximum Depth | 91% through wall | 96% through wall |

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims hereinbelow.

We claim:

1. A method for inspecting an ultrasonic reflector in a material with non-destructive ultrasound inspection which simultaneously decreases the time required for inspection and also improves the quality of inspection, comprising the steps of:

moving an ultrasonic transducer relative to said material through a range of positions within two axes of motion;

firing said ultrasonic transducer at precise locations within said range of positions;

receiving an ultrasonic echo from said material responsive to said firing;

converting said received ultrasonic echo to a received echo electrical signal having an amplitude representing a strength of said received ultrasonic echo;

measuring a time difference between said firing and said receiving;

displaying a two-dimensional map of said material in a planar C-scan view by displaying a time-gated plot of one of said two axes against the other of said two axes, and using a coding scheme to identify relative received echo electrical signal amplitudes within said plot;

determining a reflector region of interest, said reflector region of interest having a first axial starting locations of said fault on a first axis, a first axial ending location of said fault on said first axis, a second axial starting location of said fault on a second axis, and a second axial ending location of said fault on said second axis; and plotting said received echo signal data within said reflector region of interest using said second axis position plotted against said time difference, using said coding scheme to identify relative received echo electrical signal amplitudes within said plot to thereby produce a D-scan.

2. The method for inspecting a reflector in a material with non-destructive ultrasound inspection of claim 1, further comprising the steps of:

selecting a starting location of said reflector which represents a singular index position; and mapping said received echo signal data first axis plotted against said time difference for instances where said received echo signal is received at said singular index value, and using a coding scheme to identify relative received echo electrical signal amplitudes within said map, to thereby produce a B-scan.

3. The method for inspecting a reflector in a material with non-destructive ultrasound inspection of claim 2, further comprising the step of presenting said singular index position in said D-scan as an index cursor position.

4. The method for inspecting a reflector in a material with non-destructive ultrasound inspection of claim 2, further comprising the step of evaluating said B-scan for information, wherein said information includes at least one of a maximum tip signal and a fault profile.

5. The method for inspecting a reflector in a material with non-destructive ultrasound inspection of claim 4, further comprising the steps of stepping said singular index position from said second axial starting location of said reflector through a plurality of increments to said second axial ending location while simultaneously evaluating said B-scan for said information at each one of said plurality of increments.

6. The method for inspecting a reflector in a material with non-destructive ultrasound inspection of claim 5, further comprising the step of choosing a deepest one of said maximum tip signals from each of said B-scan evaluations.

7. The method for inspecting a reflector in a material with non-destructive ultrasound inspection of claim 5, further comprising the steps of:

exporting said information from said plurality of increments to a spreadsheet;

extracting depth and circumferential positions of a tip echo and a corner echo from said information; and calculating a maximum depth, reflector area, percent reflector area and length responsive to said extraction step.

8. The method for inspecting a reflector in a material with non-destructive ultrasound inspection of claim 1, further comprising the step of gating said received echo signal data from said second axis to primarily include values of said second axis that are within said reflector region of interest for operative display in said D-scan.

9. The method for inspecting a reflector in a material with non-destructive ultrasound inspection of claim 1, further comprising the step of locating an initial maximum negative response in said D-scan representative of a corner signal.

10. The method for inspecting a reflector in a material with non-destructive ultrasound inspection of claim 1, further comprising the step of locating an initial maximum positive response in said D-scan representative of a tip signal.

11. The method for inspecting a reflector in a material with non-destructive ultrasound inspection of claim 9, further comprising the step of locating an initial maximum positive response in said D-scan representative of a tip signal.

12. The method for inspecting a reflector in a material with non-destructive ultrasound inspection of claim 11, further comprising the step of estimating a maximum depth between said corner signal and said tip signal displayed in said D-scan.

13. The method for inspecting a reflector in a material with non-destructive ultrasound inspection of claim 1, further comprising the steps of:
adjusting said coding scheme to display all positive received echo electrical signal amplitudes within said plot as a single color; and
identifying a negative received echo electrical signal as a surface breaking corner signal responsive to said adjusting step.

14. The method for inspecting a reflector in a material with non-destructive ultrasound inspection of claim 1, further comprising the steps of:
adjusting said coding scheme to display all negative received echo electrical signal amplitudes within said plot as a single color; and
identifying a positive received echo electrical signal as a tip signal responsive to said adjusting step.

15. The method for inspecting a reflector in a material with non-destructive ultrasound inspection of claim 1, further comprising the step of modifying said coding scheme to non-linearly display said received echo electrical signal below a noise threshold.

16. The method for inspecting a reflector in a material with non-destructive ultrasound inspection of claim 1, further comprising the step of compressing said coding scheme for amplitudes greater than an amplitude threshold.

17. The method for inspecting a reflector in a material with non-destructive ultrasound inspection of claim 1, further comprising the step of forming a composite D-scan produced from a plurality of plots each which represent discrete locations along said first axis.

18. The method for inspecting a reflector in a material with non-destructive ultrasound inspection of claim 17, wherein said step of forming further comprises the step of rectifying and summing each unique amplitude point in said second axis and said time difference plot with corresponding points in said second axis and said time difference that have a unique location along said first axis.

19. The method for inspecting a reflector in a material with non-destructive ultrasound inspection of claim 1, further comprising the step of calculating a travel distance of said ultrasonic echo within said material from said time difference, ultrasonic wave angle, and material velocity.

20. The method for inspecting a reflector in a material with non-destructive ultrasound inspection of claim 1, further comprising the steps of:
discerning a reflector location and a general reflector direction relative to said two axes; and
defining a scan direction parallel to said general reflector direction, wherein said first axis is co-axial with said scan direction, and an index direction perpendicular thereto, wherein said second axis is co-axial with said index direction.

21. The method for inspecting a reflector in a material with non-destructive ultrasound inspection of claim 1, further comprising the step of transmitting said received echo signal to a signal processor.

22. A method for analyzing recorded ultrasound data obtained from recording time-delayed echo signals while scanning a distance along at least one axis, comprising the steps of:
representing said recorded ultrasound data using said at least one axis position as one of an abscissa or an ordinate on a Cartesian graph;
depicting a magnitude of said time delay as another of said abscissa or said ordinate different from said one of said abscissa or ordinate on a Cartesian graph;
plotting said recorded ultrasound data using said at least one axis position representation and said time difference depiction, and
color coding a relative amplitude of said recorded ultrasound data within said plot.

23. The method for analyzing recorded ultrasound scan data of claim 22, further comprising the steps of:
repeating said representing, depicting and plotting steps for each of a plurality of discrete positions along a second axis; and
forming a composite plot by the additional steps of summing points having matching abscissas and ordinates on each of said Cartesian graphs produced in said repeating step and subsequently color coding a relative amplitude of said summed points.

24. The method for analyzing recorded ultrasound scan data of claim 23, wherein said step of forming further comprises the step of rectifying each unique amplitude point in each of said Cartesian graphs prior to said summing.

25. The method for analyzing recorded ultrasound scan data of claim 22, further comprising the steps of:
adjusting said color coding to display all positive recorded ultrasound data within said plot as a single color;
identifying a negative recorded ultrasound data signal as a surface breaking corner signal responsive to said adjusting step;
altering said color coding to display all negative recorded ultrasound data within said plot as a single color; and
discerning a positive recorded ultrasound data as a tip signal responsive to said altering step.

26. The method for analyzing recorded ultrasound scan data of claim 22, further comprising the step of modifying said color coding to discontinuously display said recorded ultrasound scan data to not display below a noise threshold.

27. The method for analyzing recorded ultrasound scan data of claim 22, further comprising the steps of:
selecting a location which represents a singular distance along a first axis of said at least one axis;

mapping a second axis of said at least one axis as one of an abscissa or an ordinate on a second Cartesian graph of said recorded ultrasound scan data and said time difference as another of said abscissa or said ordinate for instances where said received echo signal is received at said singular distance, color coding a relative amplitude of said recorded ultrasound scan data within said map; and evaluating said map for information, wherein said information includes at least one of a maximum tip signal and a reflector profile.

28. A method for inspecting heat exchanger tubing at discrete times prior to installation and in-situ, comprising the steps of:

moving an ultrasonic transducer helically through said tubing;

generating ultrasonic pulses at a plurality of circumferential and axial locations during said moving;

receiving ultrasonic echoes from said tubing responsive to said pulse generating;

converting said received ultrasonic echoes to an echo electrical signal having an amplitude representing a strength of said received ultrasonic echoes;

transmitting said echo electrical signal to a signal processor;

measuring a time difference between said generating and said receiving steps;

translating said measured time difference into an equivalent material depth within said heat exchanger tubing by using said signal processor, a known ultrasonic wave angle-of-incidence, and a known ultrasonic wave velocity within said tubing;

displaying a two-dimensional map of said tubing in a planar C-scan view by displaying an ultrasonic wave transit distance gated plot of said circumferential angle against axial displacement;

correlating a visual characteristic of said two dimensional map relative amplitude to operatively enable a viewer to identify echo electrical signal amplitudes within said map;

determining an extent of a reflector within said tubing, said extent having a starting angle of said fault on a circumference of said tubing, an ending angle of said fault on said circumference, an axial starting location of said reflector on a longitudinal axis of said tubing, and an axial ending location of said reflector on said longitudinal axis;

plotting said echo electrical signal using said circumference angle plotted against said ultrasonic wave transit distance to thereby produce a D-scan;

conforming a visual characteristic of said D-scan to a relative amplitude of said echo electrical signal to operatively enable a viewer to identify echo electrical signal amplitudes within said D-scan;

selecting a starting location of said reflector which represents a singular axial position;

mapping said echo electrical signal circumferential angle plotted against said ultrasonic wave transit distance for all events where said received echo is received from said singular axial position to thereby produce a B-scan; and matching a visual feature with echo electrical signal amplitudes within said B-scan to operatively enable a viewer to identify echo electrical signal amplitudes therein.

29. The method for inspecting heat exchanger tubing of claim 28 further comprising the step of presenting said singular axial position in said D-scan as an index cursor position.

30. The method for inspecting heat exchanger tubing of claim 28 further comprising the step of evaluating said B-scan for information, wherein said information includes at least one of a maximum tip signal and a fault profile.

31. The method for inspecting heat exchanger tubing of claim 28 further comprising the step of stepping said singular axial position from said axial starting location of said fault through a plurality of increments to said axial ending location while simultaneously evaluating said B-scan for said information at each one of said plurality of increments.

32. The method for inspecting heat exchanger tubing of claim 28 further comprising the step of gating said echo electrical signal from said axial displacement to primarily include values of said axial displacement that are within said reflector extent for operative display in said D-scan.

33. The method for inspecting heat exchanger tubing of claim 28 further comprising the step of forming a composite D-scan produced from a plurality of plots each which represent discrete locations along said tubing circumference.

34. The method for inspecting heat exchanger tubing of claim 28 further comprising the step of forming a composite B-scan produced from a plurality of plots each which represent discrete locations along said tubing axial length.

35. The method for inspecting heat exchanger tubing of claim 28 further comprising the step of forming a composite C-scan produced from a plurality of plots, each which represent discrete time differences.

36. The method for inspecting heat exchanger tubing of claim 28 wherein said steps of moving, generating, receiving, converting, transmitting, measuring, translating, displaying, correlating, determining, plotting, confirming, selecting, mapping and matching are performed on said heat exchanger tubing prior to installation, and then repeated in-situ.

37. The method for inspecting heat exchanger tubing of claim 36 further comprising the steps of:

assessing whether said heat exchanger tubing is suitable for a heat exchanger operation; and replacing said heat exchanger tubing responsive to said tubing not being deemed suitable in said assessing step.

* * * * *